United States Patent
Horvath et al.

(10) Patent No.: US 7,867,995 B2
(45) Date of Patent: *Jan. 11, 2011

(54) βD-CRYSTALLINE FORM OF IVABRADINE HYDROCHLORIDE, A PROCESS FOR ITS PREPARATION AND PHARMACEUTICAL COMPOSITIONS CONTAINING IT

(75) Inventors: Stephane Horvath, La Chapelle-Saint-Mesmin (FR); Marie-Noelle Auguste, Orleans (FR); Gerard Damien, Meung-sur-Loire (FR)

(73) Assignee: Les Laboratoires Servier, Suresnes Cedex (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/583,857

(22) Filed: Aug. 27, 2009

(65) Prior Publication Data

US 2009/0318416 A1    Dec. 24, 2009

Related U.S. Application Data

(63) Continuation of application No. 12/072,577, filed on Feb. 27, 2008, now abandoned, which is a continuation of application No. 11/359,263, filed on Feb. 22, 2006, now Pat. No. 7,361,652.

(30) Foreign Application Priority Data

Feb. 28, 2005   (FR)   ................................. 05 01987

(51) Int. Cl.
C07D 223/16   (2006.01)
A61K 31/55    (2006.01)
A61P 9/10     (2006.01)

(52) U.S. Cl. .................................. 514/212.07; 540/523
(58) Field of Classification Search ................. 540/523; 514/212.07

See application file for complete search history.

(56) References Cited

FOREIGN PATENT DOCUMENTS

EP   0534859   3/1993

OTHER PUBLICATIONS

Preliminary Search Report for French National Application FR0501987, Aug. 24, 2005.
Ferrari, et al., *European Heart Journal Supplements*, 2005, 7 (Supplement H), H16-H21.
Fox, *European Heart Journal Supplements*, 2005, 7 (Supplement H), H33-H36.

*Primary Examiner*—Bruck Kifle
(74) *Attorney, Agent, or Firm*—Hueschen and Sage

(57) ABSTRACT

A βd-Crystalline form of ivabradine hydrochloride of formula (I):

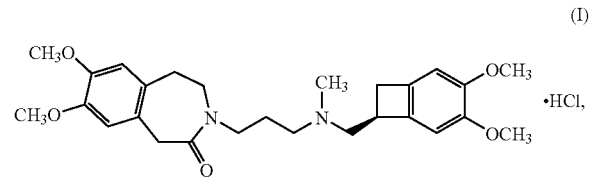

(I)

characterised by its powder X-ray diffraction data.

Medicinal products containing the same which are useful as bradycardics.

8 Claims, No Drawings

βD-CRYSTALLINE FORM OF IVABRADINE HYDROCHLORIDE, A PROCESS FOR ITS PREPARATION AND PHARMACEUTICAL COMPOSITIONS CONTAINING IT

The present invention relates to the new βd-crystalline form of ivabradine hydrochloride of formula (I), to a process for its preparation and to pharmaceutical compositions containing it.

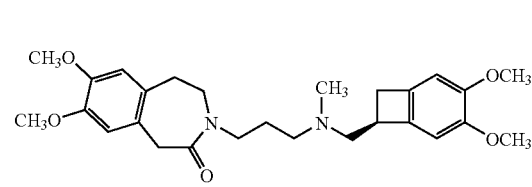

Ivabradine, and addition salts thereof with a pharmaceutically acceptable acid, and more especially its hydrochloride, have very valuable pharmacological and therapeutic properties, especially bradycardic properties, making those compounds useful in the treatment or prevention of various clinical situations of myocardial ischaemia such as angina pectoris, myocardial infarct and associated rhythm disturbances, and also in various pathologies involving rhythm disturbances, especially supraventricular rhythm disturbances, and in heart failure.

The preparation and therapeutic use of ivabradine and addition salts thereof with a pharmaceutically acceptable acid, and more especially its hydrochloride, have been described in the European patent specification EP 0 534 859.

In view of the pharmaceutical value of this compound, it has been of prime importance to obtain it with excellent purity. It has also been important to be able to synthesise it by means of a process that can readily be converted to the industrial scale, especially in a form that allows rapid filtration and drying. Finally, that form had to be perfectly reproducible, easily formulated and sufficiently stable to allow its storage for long periods without particular requirements for temperature, light or oxygen level.

The patent specification EP 0 534 859 describes a synthesis process for ivabradine and its hydrochloride. However, that document does not specify the conditions for obtaining ivabradine in a form that exhibits those characteristics in a reproducible manner.

The Applicant has now found that a particular salt of ivabradine, the hydrochloride, can be obtained in a crystalline form that is well defined and that exhibits valuable characteristics of stability and processability.

More specifically, the present invention relates to the βd-crystalline form of ivabradine hydrochloride, which is characterised by the following powder X-ray diffraction diagram measured using a PANalytical X'Pert Pro diffractometer together with an X'Celerator detector and expressed in terms of ray position (Bragg's angle 2 theta, expressed in degrees), ray height (expressed in counts), ray area (expressed in counts×degrees), ray width at half-height ("FWHM", expressed in degrees) and interplanar distance d (expressed in Å):

| Ray no. | Angle 2 theta (degrees) | Height (counts) | Area (counts × degrees) | FWHM (degrees) | Interplanar distance (Å) |
|---|---|---|---|---|---|
| 1 | 4.0 | 244 | 80 | 0.3346 | 22.139 |
| 2 | 5.9 | 377 | 56 | 0.1506 | 14.829 |
| 3 | 6.9 | 94 | 50 | 0.5353 | 12.835 |
| 4 | 9.2 | 1975 | 293 | 0.1506 | 9.623 |
| 5 | 11.8 | 136 | 27 | 0.2007 | 7.473 |
| 6 | 12.5 | 1826 | 241 | 0.1338 | 7.083 |
| 7 | 13.6 | 1834 | 303 | 0.1673 | 6.491 |
| 8 | 14.5 | 51 | 20 | 0.4015 | 6.119 |
| 9 | 16.0 | 1441 | 214 | 0.1506 | 5.525 |
| 10 | 17.3 | 4472 | 738 | 0.1673 | 5.134 |
| 11 | 18.4 | 546 | 108 | 0.2007 | 4.808 |
| 12 | 19.6 | 1025 | 169 | 0.1673 | 4.524 |
| 13 | 20.0 | 688 | 91 | 0.1338 | 4.448 |
| 14 | 20.4 | 1027 | 186 | 0.184 | 4.362 |
| 15 | 21.4 | 102 | 24 | 0.2342 | 4.143 |
| 16 | 22.3 | 1903 | 283 | 0.1506 | 3.990 |
| 17 | 22.8 | 674 | 89 | 0.1338 | 3.897 |
| 18 | 23.0 | 623 | 62 | 0.1004 | 3.866 |
| 19 | 24.4 | 845 | 56 | 0.0669 | 3.647 |
| 20 | 25.0 | 3749 | 557 | 0.1506 | 3.554 |
| 21 | 25.5 | 512 | 84 | 0.1673 | 3.497 |
| 22 | 26.6 | 289 | 76 | 0.2676 | 3.346 |
| 23 | 28.3 | 275 | 91 | 0.3346 | 3.151 |
| 24 | 29.1 | 126 | 21 | 0.1673 | 3.066 |

The invention relates also to a process for the preparation of the βd-crystalline form of ivabradine hydrochloride, which process is characterised in that a mixture of ivabradine hydrochloride and water or a mixture of ivabradine hydrochloride, isopropanol and water is heated until dissolution is complete and is then progressively cooled until crystallisation is complete, and the crystals thereby formed are collected and dehydrated.

In the crystallisation process according to the invention it is possible to use ivabradine hydrochloride obtained by any process, for example ivabradine hydrochloride obtained by the preparation process described in patent specification EP 0 534 859.

The solution may advantageously be seeded during the cooling step.

The invention relates also to pharmaceutical compositions comprising as active ingredient the βd-crystalline form of ivabradine hydrochloride together with one or more appropriate, inert, non-toxic excipients. Among the pharmaceutical compositions according to the invention, there may be mentioned more especially those that are suitable for oral, parenteral (intravenous or subcutaneous) or nasal administration, tablets or dragées, sublingual tablets, gelatin capsules, lozenges, suppositories, creams, ointments, dermal gels, injectable preparations, drinkable suspensions.

The useful dosage can be varied according to the nature and severity of the disorder, the administration route and the age and weight of the patient. That dosage varies from 1 to 500 mg per day in one or more administrations.

The following Examples illustrate the invention.

The X-ray powder diffraction spectrum was measured under the following experimental conditions:
PANalytical X'Pert Pro diffractometer, X'Celerator detector, temperature-regulated chamber,
voltage 45 kV, intensity 40 mA,
mounting θ-θ,
nickel (Kβ) filter,
incident-beam and diffracted-beam Soller slit: 0.04 rad,
fixed angle of divergence slits: ⅛°,
mask: 10 mm, antiscatter slit: ¼°, measurement mode: continuous from 3° to 30°, in increments of 0.017°, measurement time per step: 19.7 s, total time : 4 min 32 s, measurement speed: 0.108°/s, measurement temperature : ambient.

EXAMPLE 1

βd-Crystalline Form of Ivabradine Hydrochloride 720 ml of purified water are preheated to 50° C., and then 250 g of ivabradine hydrochloride obtained according to the process described in the patent specification EP 0 534 859 are added in portions, with stirring, and the mixture is heated at 74° C. until dissolution is complete. The resulting clear solution is heated for 2 more hours at 74° C. and is then progressively cooled, first to 40° C., and then to ambient temperature. The solution is subsequently stored at ambient temperature for 2 days, and then the solid suspension is spread out in a thin layer on a crystallisation plate. The excess water is driven off under a gentle current of nitrogen.

The product thereby obtained is dehydrated by progressively heating at a rate of 5° C./min up to a temperature of 80° C.

X-Ray Powder Diffraction Diagram:

The X-ray powder diffraction profile (diffraction angles) of the βd-form of ivabradine hydrochloride is given by the significant rays collated in the following table:

| Ray no. | Angle 2 theta (degrees) | Height (counts) | Area (counts × degrees) | FWHM (degrees) | Interplanar distance (Å) |
|---|---|---|---|---|---|
| 1 | 4.0 | 244 | 80 | 0.3346 | 22.139 |
| 2 | 5.9 | 377 | 56 | 0.1506 | 14.829 |
| 3 | 6.9 | 94 | 50 | 0.5353 | 12.835 |
| 4 | 9.2 | 1975 | 293 | 0.1506 | 9.623 |
| 5 | 11.8 | 136 | 27 | 0.2007 | 7.473 |
| 6 | 12.5 | 1826 | 241 | 0.1338 | 7.083 |
| 7 | 13.6 | 1834 | 303 | 0.1673 | 6.491 |
| 8 | 14.5 | 51 | 20 | 0.4015 | 6.119 |
| 9 | 16.0 | 1441 | 214 | 0.1506 | 5.525 |
| 10 | 17.3 | 4472 | 738 | 0.1673 | 5.134 |
| 11 | 18.4 | 546 | 108 | 0.2007 | 4.808 |
| 12 | 19.6 | 1025 | 169 | 0.1673 | 4.524 |
| 13 | 20.0 | 688 | 91 | 0.1338 | 4.448 |
| 14 | 20.4 | 1027 | 186 | 0.184 | 4.362 |
| 15 | 21.4 | 102 | 24 | 0.2342 | 4.143 |
| 16 | 22.3 | 1903 | 283 | 0.1506 | 3.990 |
| 17 | 22.8 | 674 | 89 | 0.1338 | 3.897 |
| 18 | 23.0 | 623 | 62 | 0.1004 | 3.866 |
| 19 | 24.4 | 845 | 56 | 0.0669 | 3.647 |
| 20 | 25.0 | 3749 | 557 | 0.1506 | 3.554 |
| 21 | 25.5 | 512 | 84 | 0.1673 | 3.497 |
| 22 | 26.6 | 289 | 76 | 0.2676 | 3.346 |
| 23 | 28.3 | 275 | 91 | 0.3346 | 3.151 |
| 24 | 29.1 | 126 | 21 | 0.1673 | 3.066 |

EXAMPLE 2

Pharmaceutical Composition

Formula for the preparation of 1000 tablets each containing 5 mg of ivabradine base:

| | |
|---|---|
| Compound of Example 1 | 5.39 g |
| Maize starch | 20 g |
| Anhydrous colloidal silica | 0.2 g |
| Mannitol | 63.91 g |
| PVP | 10 g |
| Magnesium stearate | 0.5 g |

The invention claimed is:

1. A βd-Crystalline form of ivabradine hydrochloride of formula (I):

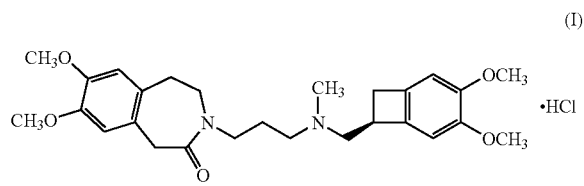

(I)

having a powder X-ray diffraction diagram exhibiting peaks at 9.2 and 13.6 deg 2 theta.

2. A βd-Crystalline form of ivabradine hydrochloride of formula (I):

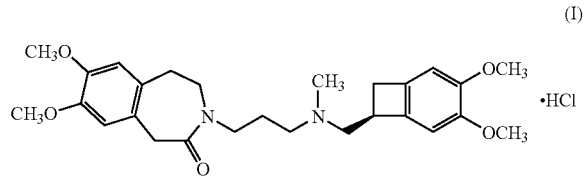

(I)

having a powder X-ray diffraction diagram exhibiting peaks at 9.2, 12.5, 13.6, 17.3, 22.3 and 25.0 deg 2 theta.

3. A solid pharmaceutical composition comprising as active ingredient the βd-crystalline form of ivabradine hydrochloride of claim 1, in combination with one or more pharmaceutically acceptable, inert, non-toxic carriers.

4. A method for treating a condition selected from angina pectoris, myocardial infarct, and heart failure, such method comprising administering to a living animal body a therapeutically effective amount of the βd-crystalline form of ivabradine hydrochloride of claim 1.

5. A solid pharmaceutical composition comprising as active ingredient the βd-crystalline form of ivabradine hydrochloride of claim 2, in combination with one or more pharmaceutically acceptable, inert, non-toxic carriers.

6. A method for treating a condition selected from angina pectoris, myocardial infarct, and heart failure, such method comprising administering to a living animal body a therapeutically effective amount of the βd-crystalline form of ivabradine hydrochloride of claim 2.

7. The method of claim 4, wherein the living animal body is a human.

8. The method of claim 6, wherein the living animal body is a human.

* * * * *